(12) United States Patent
Roux et al.

(10) Patent No.: US 7,947,675 B2
(45) Date of Patent: May 24, 2011

(54) TRIFLUOROMETHYLBENZAMIDE DERIVATIVES AND THERAPEUTIC USES THEREOF

(75) Inventors: Bruno Roux, Lyons (FR); Isabelle Berard, Villard les Dombes (FR)

(73) Assignee: Merck Patent GmbH, Darmstadt (DE)

( * ) Notice: Subject to any disclaimer, the term of this patent is extended or adjusted under 35 U.S.C. 154(b) by 731 days.

(21) Appl. No.: 11/908,712

(22) PCT Filed: Feb. 16, 2006

(86) PCT No.: PCT/EP2006/001374
§ 371 (c)(1),
(2), (4) Date: Sep. 14, 2007

(87) PCT Pub. No.: WO2006/097169
PCT Pub. Date: Sep. 21, 2006

(65) Prior Publication Data
US 2008/0119459 A1 May 22, 2008

(30) Foreign Application Priority Data
Mar. 14, 2005 (FR) ..................... 05 02479

(51) Int. Cl.
| | |
|---|---|
| *A61K 31/497* | (2006.01) |
| *A61K 31/00* | (2006.01) |
| *A61K 31/55* | (2006.01) |
| *A61K 31/54* | (2006.01) |
| *A61K 31/535* | (2006.01) |
| *A61K 31/435* | (2006.01) |
| *A61K 31/445* | (2006.01) |
| *A61K 31/41* | (2006.01) |
| *A61K 31/425* | (2006.01) |
| *A61K 31/42* | (2006.01) |
| *A61K 31/415* | (2006.01) |
| *A61K 31/16* | (2006.01) |
| *A01N 43/00* | (2006.01) |
| *A01N 43/40* | (2006.01) |
| *A01N 43/64* | (2006.01) |
| *A01N 43/78* | (2006.01) |
| *A01N 43/80* | (2006.01) |
| *A01N 43/76* | (2006.01) |
| *A01N 43/50* | (2006.01) |
| *A01N 37/18* | (2006.01) |

(52) U.S. Cl. ......... 514/210.11; 514/211.01; 514/212.01; 514/226.8; 514/227.5; 514/228.8; 514/231.2; 514/277; 514/315; 514/359; 514/365; 514/372; 514/374; 514/385; 514/613; 540/484; 540/544; 540/553; 544/3; 544/53; 544/56; 544/63; 544/88; 544/98; 546/1; 548/125; 548/146; 548/206; 548/215; 548/240; 564/123

(58) Field of Classification Search .................. None
See application file for complete search history.

(56) References Cited

U.S. PATENT DOCUMENTS
6,207,671 B1 3/2001 Schmidt et al.
7,138,414 B2 11/2006 Schoenafinger et al.

FOREIGN PATENT DOCUMENTS
EP 0 818 448 A1 1/1998
WO WO 2004/007455 A 1/2004
WO WO 2004/017969 A 3/2004

OTHER PUBLICATIONS

MacLean et al. Journal of Clinical Endocrinology and Metabolism, 2005, 90(4), 2250-58.*
Forester et al. Circulation, 2005, 111, 1847-54.*
Dixit et al. BMC Endocrine Disorders, 2005, 5:7, 1-10.*
"Diabetic Neuropathy", http://www.healthscout.com/ency/68/90/main.html, accessed May 19, 2010.*
Williamson et al., Annals of Internal Medicine, 2004, 140(11), pp. 951-957.*
"Atherosclerosis", http://www.healthguidance.org/entry/4736/1/Atherosclerosis—Symptoms-Causes-Prevention-and-Treatment.html, accessed May 19, 2010.*
"Obesity: Prevention", http://www.mayoclinic.com/health/obesity/ds00314/dsection=prevention, accessed May 19, 2010.*
Viswanathan, Indian Journal of Nephrology, 2004, 14, 157-162.*
Sheibly, Journal of Organic Chemistry, 1952, 17, pp. 221-225.*
Ramratap S. Kushwaha et al., "Characterization of cholesteryl ester transfer protein inhibitor from plasma of baboons," Journal of Lipid Research, vol. 34, 1993, pp. 1285-1297, XP002347987.

* cited by examiner

*Primary Examiner* — Noble Jarrell
(74) *Attorney, Agent, or Firm* — Millen, White, Zelano & Branigan, P.C.

(57) ABSTRACT

Compounds of the formula (I), in which the radicals $R^1$ to $R^3$ and AR are as defined in the description, processes for the preparation thereof, the use thereof in the treatment of cardiovascular diseases, and pharmaceutical compositions comprising them.

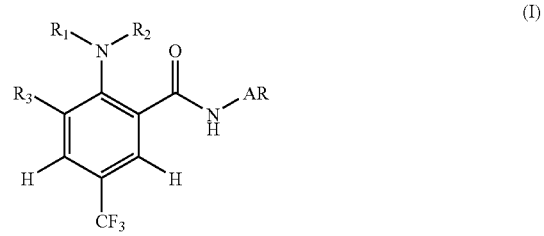

(I)

20 Claims, 3 Drawing Sheets

Figure 1

SCHEME 1

Figure 2

SCHEME 2

Figure 3

SCHEME 3

TRIFLUOROMETHYLBENZAMIDE DERIVATIVES AND THERAPEUTIC USES THEREOF

The present invention relates to trifluoromethylbenzamide derivatives, to processes for the preparation of these derivatives, to pharmaceutical compositions or medicaments comprising these derivatives, and also to treatment or prevention methods, and to the use of these derivatives as repressors of cholesterol ester transfer protein, CETP, for the prevention and treatment of cardiovascular diseases, and in particular atherosclerosis, dyslipidaemia and type II diabetes.

Atherosclerosis, and cardiovascular diseases in general, are one of the main causes of death in developed countries. Despite the efforts directed towards minimising the risk factors, such as smoking, a sedentary lifestyle and a poorly balanced diet, and also therapeutic treatments for dyslipidaemia using pharmaceutical compositions, death caused by myocardial infarction and other cardiovascular diseases remains very high.

It has been demonstrated that the risks of cardiovascular diseases are highly dependent on the levels of low-density lipoproteins (LDL) in the blood plasma.

Whereas high levels of cholesterol LDL and triglycerides contribute towards the risks of developing cardiovascular diseases, high levels of cholesterol high-density lipoproteins (HDL) reduce these risks. Thus, dyslipidaemia does not have only one risk profile for cardiovascular diseases, but rather may encompass one or more lipid dysfunctions.

Among the many factors acting on the levels of triglycerides, LDL and HDL, CETP (cholesteryl ester transfer protein) plays an important role. CETP catalyses the transfer and exchange of cholesterol esters and triglycerides between the HDLs of the plasma and the low-density lipoproteins (LDLs) and very-low-density lipoproteins (VLDLs) that contain triglycerides. The action of CETP on the levels of these various lipids contained in the lipoproteins is increased, and considered as pro-atherogenic in individuals in whom the lipid profile represents a high risk of cardiovascular diseases.

Thus, modulating the activity of CETP, either by direct inhibition or by controlled regulation of the expression of CETP, may be considered as a possible means of therapeutic treatment (see, for example, Kushwaha et al., *J. Lipid Research*, 34, (1993), 1285-1297).

This is why considerable research efforts have been directed towards CETP inhibitors, and have given rise to inhibitors of peptide and non-peptide type. Among the latter, mention may be made of CETP inhibitors of tetrahydroquinoline type (EP-A-0 818 448) or those of 2-arylpyridine type (EP-A-0 796 846), or alternatively those described in EP-A-0 818 197, to mention but a few.

Despite the existence in the literature of these various inhibitors, it is still of major interest to have available novel, more efficient, more specific CETP inhibitors, having a longer duration of action, better absorption and better solubility in biological media, and showing fewer risks of side effects.

The Applicant proposes to achieve these objectives, in total or in part, by means of compounds of trifluoromethylbenzamide structure. A certain number of trifluoromethylbenzamides have been described, but none of the literature data suggests that such derivatives can have an effect on CETP and thus be useful in the treatment of cardiovascular diseases:

*J. Med. Chem.*, 12, pp. 299-303, (1969):
α,α,α-Trifluorotoluamides as anticoccidial agents
FR 2 329 266: Nouveaux amino-benzamides, leurpréparation et leur utilisation en tant que médicaments [Novel aminobenzamides, preparation thereof and use thereof as medicaments]

*Pharmazie* 37, H, 6, pp. 413-415 (1982): Synthesis of substituted benzamides and benzimidazoles as anthelmintic and antimicrobial agents

EP 947 500: Sulfonamide and carboxamide derivatives and drugs comprising the same as the active ingredient FR 2 838 739: Preparation of N-[phenyl(piperid-2-yl)methyl]benzamides as specific inhibitors of glycine transporters glyt1 and/or glyt2

WO9206964: Preparation of pyrimidinoylbenzamides and analogs as acaricides and insecticides Surprisingly, the Applicant has identified novel trifluoromethylbenzamide derivatives that allow these objectives to be achieved.

More specifically, the present invention relates to benzamide derivatives of the formula (I):

in which:

R$_1$ and R$_2$, which may be identical or different, are a (C$_1$-C$_6$)alkyl radical or a (C$_3$-C$_{10}$)cycloalkyl radical, or alternatively the two radicals R$_1$ and R$_2$ together form, with the nitrogen atom that bears them, a saturated heterocyclic radical of the formula (II):

in which:

Y and Z, which may be identical or different, are C$_1$, C$_2$ or C$_3$ hydrocarbon-based chains, optionally substituted by one or more radicals R$_4$, which may be identical or different, chosen from (C$_1$-C$_6$)alkyl and (C$_3$-C$_{10}$)cycloalkyl, X is a carbon, oxygen or sulfur atom, a group >CR$_6$R$_7$ with R$_6$ and R$_7$, which may be identical or different, representing OH, a group —COOAlk, Alk meaning C$_1$-C$_6$ alkyl, preferably a —COOMe group, a —CH$_2$OH group, a substituted or unsubstituted (C$_6$-C$_{18}$)aryl radical, a substituted or unsubstituted (C$_6$-C$_{18}$)aroyl radical, a group N—R$_5$ with R$_5$ being a (C$_1$-C$_6$)alkyl radical, or alternatively the two radicals R$_1$ and R$_2$ together form, with the nitrogen atom that bears them, a tetrahydroisoquinolyl radical R$_3$ is NO$_2$, NH$_2$, CN, Cl or Br AR is a substituted or unsubstituted $(C_6-C_{18})$aryl radical of the formula (III):

(III)

in which $R_8$, $R_9$, $R_{10}$, $R_{11}$ and $R_{12}$, which may be identical or different, are chosen from a hydrogen atom, a halogen atom, a branched or unbranched $(C_1-C_{10})$alkyl radical, a substituted or unsubstituted aryl radical, a CN radical and a trifluoromethyl group, or alternatively $R_8$ and $R_9$ or $R_9$ and $R_{10}$ or $R_{10}$ and $R_{11}$ or $R_{11}$ and $R_{12}$ together form a chain —$(CH_2)_p$— with p=1-5, the optical and geometrical isomers, oxide forms, solvates and tautomeric forms thereof, and also the pharmaceutically acceptable addition salts thereof with acids or bases.

The acids that can be used to form salts of compounds of the formula (I) are mineral or organic acids. The resulting salts are, for example, the hydrochlorides, hydrobromides, sulfates, hydrogen sulfates, dihydrogen phosphates, citrates, maleates, fumarates, trifluoroacetates, 2-naphthalenesulfonates and para-toluenesulfonates.

The invention especially covers the pharmaceutically acceptable salts, but also salts that allow a suitable separation or crystallisation of the compounds of the formula (I), such as the salts obtained with chiral acids.

Examples of chiral acids that can be used include (+)-D-di-O-benzoyltartaric acid, (−)-L-di-O-benzoyltartaric acid, (−)-di-O,O'-p-toluoyl-L-tartaric acid, (+)-di-O,O'-p-toluoyl-D-tartaric acid, (R)-(+)-malic acid, (S)-(−)-malic acid, (+)-camphanic acid, (−)-camphanic acid, R(−)-1,1'-binaphthalene-2,2'-diyl hydrogen phosphate, (S)-(+)-1,1'-binaphthalene-2,2'-diyl hydrogen phosphate, (+)-camphoric acid, (−)-camphoric acid, (S)-(+)-2-phenylpropionic acid, (R)-(−)-2-phenylpropionic acid, D-(−)-mandelic acid, L-(+)-mandelic acid, D-tartaric acid and L-tartaric acid, or a mixture of two or more thereof.

The invention also covers the optical isomers, in particular stereoisomers and diastereoisomers, where appropriate, of the compounds of the formula (I), and also mixtures of optical isomers in all proportions, including racemic mixtures.

The geometrical isomers, commonly known as cis and trans isomers, are also included in the field of the present invention, in pure forms or as mixtures in all proportions.

Depending on the nature of the substituents, the compounds of the formula (I) may also be in various tautomeric forms that are also included in the present invention, alone or as mixtures of two or more thereof, in all proportions.

The compounds of the formula (I) above also include the prodrugs of these compounds.

The term "prodrugs" means compounds which, once administered to the patient, are chemically and/or biologically converted in the live body, into compounds of the formula (I).

In the present description hereinbelow, the term "$(C_1-C_6)$ alkyl radical" means a linear or branched hydrocarbon-based chain containing from 1 to 6 carbon atoms.

Examples of $(C_1-C_6)$alkyl radicals are methyl, ethyl, propyl, isopropyl, butyl, isobutyl, tert-butyl, pentyl, isopentyl, neopentyl, methylbutyl, ethylpropyl, hexyl, isohexyl, neohexyl, methylpentyl, dimethylbutyl, ethylbutyl and methylethylpropyl.

The term $(C_3-C_{10})$cycloalkyl radical denotes a mono-, bi- or polycyclic hydrocarbon-based radical containing from 3 to 10 carbon atoms. Examples of $C_3-C_{10}$ cycloalkyl radicals are especially cyclopropyl, cyclobutyl, cyclopentyl, cyclohexyl, cycloheptyl, cyclooctyl and cyclodecyl radicals.

Still within the context of the present invention, the term "$(C_6-C_{18})$aryl radical" means a mono-, bi- or polycyclic aromatic radical containing from 6 to 18 carbon atoms. Aryl radicals that may be mentioned include phenyl, naphthyl, anthryl and phenanthryl radicals.

Still within the context of the present invention, the term "$(C_6-C_{18})$aroyl radical" means a radical of the type $(C_6-C_{18})$aryl-C(=O)—, $(C_6-C_{18})$aryl having the same definition as above. $(C_6-C_{18})$Aroyl radicals that may be mentioned include benzoyl, naphthoyl, anthroyl and phenanthroyl radicals.

Saturated or unsaturated, 5- to 8-membered monocyclic heterocycles are the saturated or, respectively, the unsaturated derivatives of the aromatic heterocycles.

More particularly, mention may be made of morpholine, piperidine, thiazolidine, oxazolidine, tetrahydrothienyl, tetrahydrofuryl, pyrrolidine, isoxazolidine, imidazolidine, tetrahydroquinoline and pyrazolidine, and more particularly:

The various aryl groups and radicals defined in the present description are optionally substituted by one or more of the following radicals G:

trifluoromethyl; styryl; halogen atom; monocyclic bicyclic or tricyclic aromatic heterocyclic radical comprising one or more hetero atoms chosen from O, N and S; and optionally substituted by one or more radicals T as defined below; a group aryl-CO— in which aryl represents an aryl radical as defined above optionally substituted by one or more radicals T; nitro; cyano; $(C_1-C_{10})$alkyl; $(C_1-C_{10})$alkylcarbonyl; $(C_1-C_{10})$alkoxycarbonyl-A-in which A represents $(C_1-C_6)$alkylene, $(C_2-C_6)$alkenylene or a bond; $(C_3-C_{10})$cycloalkyl; trifluoromethoxy; di(C$_1$-C$_{10}$)alkylamino; (C$_1$-C$_{10}$)alkoxy(C$_1$-C$_{10}$)alkyl; (C$_1$-C$_{10}$)alkoxy; (C$_6$-C$_{18}$)aryl optionally substituted by one or more radicals T; (C$_6$-C$_{18}$)aryl(C$_1$-C$_{10}$)alkoxy(CO)$_n$— in which n is 0 or 1, and aryl is optionally substituted by one or more radicals T; (C$_6$-C$_{18}$)aryloxy-(CO)$_n$— in which n is 0 or 1 and in which aryl is optionally substituted by one or more radicals T; (C$_6$-C$_{18}$)arylthio in which aryl is optionally substituted by one or more radicals T; (C$_6$-C$_{18}$)aryloxy(C$_1$-C$_{10}$)alkyl(CO)$_n$— in which n is 0 or 1 and in which aryl is optionally substituted by one or more radicals T; a saturated or unsaturated, 5- to 8-membered monocyclic heterocycle comprising one or more hetero atoms chosen from O, N and S, optionally substituted by one or more radicals T; (C$_6$-C$_{18}$)arylcarbonyl optionally substituted by one or more radicals T; (C$_6$-C$_{18}$)arylcarbonyl-B—(CO)$_n$— in which n is 0 or 1; B represents (C$_1$-C$_6$)alkylene or (C$_2$-C$_6$)alkenylene and aryl is optionally substituted by one or more radicals T; (C$_6$-C$_{18}$)aryl-C—(CO)$_n$— in which n is 0 or 1, C represents (C$_1$-C$_6$)alkylene or (C$_2$-C$_6$)alkenylene and aryl is optionally substituted by one or more radicals T; (C$_6$-C$_{18}$)aryl fused to a saturated or unsaturated heterocycle as defined above optionally substituted by one or more radicals T; (C$_2$-C$_{10}$)alkynyl; T is chosen from a halogen atom; (C$_6$-C$_{18}$)aryl; (C$_1$-C$_6$)alkyl; (C$_1$-C$_6$)alkoxy; (C$_1$-C$_6$)alkoxy(C$_6$-C$_{18}$)aryl; nitro; carboxyl; (C$_1$-C$_6$)alkoxycarboxyl; and T may represent oxo if it substitutes a saturated or unsaturated heterocycle; or alternatively T represents (C$_1$-C$_6$)alkoxycarbonyl(C$_1$-C$_6$)alkyl; or (C$_1$-C$_6$)alkylcarbonyl((C$_1$-C$_6$)alkyl)$_n$- in which n is 0 or 1.

If two vicinal carbon atoms are substituted, T may represent a C$_1$-C$_6$ alkylenediyl chain or a C$_1$-C$_6$ alkylenedioxy chain.

The term "halogen atom" means a chlorine, bromine, iodine or fluorine atom.

The term "alkylenediyl chain" means a divalent radical of linear or branched aliphatic hydrocarbon-based type derived from the alkyl groups defined above by abstraction of a hydrogen atom. Preferred examples of alkylenediyl chains are the chains —(CH$_2$)$_k$— in which k represents an integer chosen from 2, 3, 4, 5 and 6 and the chains >C(CH$_3$)$_2$ and —CH$_2$—C(CH$_3$)$_2$—CH$_2$—. The alkylenedioxy chains denote chains —O-Alk-O— in which Alk represents linear or branched alkylene, it being understood that alkylene is as defined above for alkylenediyl. Preferred meanings of —O-Alk-O— are, for example, —O—C(CH$_3$)$_2$—O and —O—CH$_2$—CH$_2$—O—.

The term "alkenylene" defines an unsaturated alkylene chain containing one or more ethylenic unsaturations, preferably one to three ethylenic unsaturations. Examples of alkylene chains are —CH=CH— and —CH=CH—CH=CH—.

The term "alkynyl" means an aliphatic hydrocarbon-based group containing one or more unsaturations of acetylenic type. A preferred example is HC≡C—.

A first preferred subgroup of compounds of the invention consists of the compounds of the formula (I) for which:
R$_1$ and R$_2$ form with the nitrogen the following groups:

the other substituents being as defined above.

A second preferred subgroup of compounds of the invention consists of the compounds of the formula (I) for which:
R$_3$ is NO$_2$, NH$_2$, CN, Cl or Br:
the other substituents being as defined above.

A third preferred subgroup of compounds of the invention consists of the compounds of the formula (I) for which:
AR is a radical of the formula (III):

with R$_8$, R$_9$ and R$_{12}$ representing hydrogen;
and R$_{10}$ and R$_{11}$ representing chlorine;
the other substituents being as defined above.

According to one embodiment, the compounds of the invention are those that combine the characteristics of these three subgroups.

More particularly, the preferred compounds are those of the formula (I) chosen from:
- N-(3,4-dichlorophenyl)-3-nitro-2-piperid-1-yl-5-trifluoromethylbenzamide;
- 3-amino-N-(3,4-dichlorophenyl)-2-piperid-1-yl-5-trifluoromethylbenzamide;
- 3-bromo-N-(3,4-dichlorophenyl)-2-piperid-1-yl-5-trifluoromethylbenzamide;
- 3-cyano-N-(3,4-dichlorophenyl)-2-piperid-1-yl-5-trifluoromethylbenzamide;
- 2-azepan-1-yl-3-chloro-N-(3,4-dichlorophenyl)-5-trifluoromethylbenzamide;
- 3-chloro-N-(3,4-dichlorophenyl)-2-(4-methylpiperid-1-yl)-5-trifluoromethylbenzamide;
- 3-chloro-N-(3,4-dichlorophenyl)-2-(4-hydroxy-4-phenylpiperid-1-yl)-5-trifluoromethylbenzamide;

methyl-1-[2-chloro-6-(((3,4-dichlorophenyl)amino)carbonyl)-4-(trifluoromethyl)phenyl]piperidine-4-carboxylate;

3-chloro-N-(3,4-dichlorophenyl)-2-(4-hydroxymethylpiperid-1-yl)-5-trifluoromethylbenzamide;

3-chloro-N-(3,4-dichlorophenyl)-2-(3,5-dimethylpiperid-1-yl)-5-trifluoromethylbenzamide;

3-chloro-N-(3,4-dichlorophenyl)-2-(octahydroisoquinol-2(1H)yl)-5-trifluoromethylbenzamide.

The invention also relates to pharmaceutical compositions or medicaments comprising a pharmaceutically effective amount of at least one compound of the formula (I) (active principle) as defined above in combination with one or more pharmaceutically acceptable vehicles or excipients.

According to a first embodiment, these compositions are in solid form and may take any usual unit or dispersed form. The term "unit form" means a conformation, such as a tablet, a gel capsule or the like. The term "dispersed form" means any pulverulent, granular or similar form. These various solid forms, for example tablet, gel capsule, powder or granule, may be of the immediate-release type or of the controlled- or delayed-release type. These compositions or medicaments in solid form are generally intended for oral use, optionally after diluting or dissolving in a liquid vehicle or excipient. However, in particular for the pulverulent or granular forms, these compositions or medicaments may be intended for administration via other routes, such as the parenteral route, preferably the intravenous route, in the form of a solution for injection after dissolution or dispersion in a liquid excipient or vehicle, or via the local or topical route, after dissolution or dispersion in a suitable pharmaceutical form, for example a solution, cream, pomade, gel or the like for local or topical application. It may also be envisaged to incorporate such a composition or medicament into a device or other product, which is preferably adhesive, for application to the skin, preferably in order to administer the active principle through the skin (for example a transdermal patch).

The pharmaceutical compositions or medicaments according to the invention may also, according to a second embodiment, be directly in the form of a solution for oral administration, a solution especially for parenteral and preferably intravenous injection, or alternatively in the form of a solution, cream, pomade, gel or the like, or alternatively in any form of product or device for topical or local application, the active principle possibly being dissolved or dispersed in these compositions.

According to one embodiment, a solid composition, e.g. for oral administration, is prepared by adding to the active principle a filler and, optionally, a binder, a disintegrant, a lubricant, a dye and/or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide; examples of binders include poly(vinyl alcohol), poly(vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The dye may be any dye permitted for use in medicaments. Examples of flavour enhancers include cocoa powder, mint in herb form, aromatic powder, mint in oil form, borneol and cinnamon powder. Needless to say, the tablet or granule may be suitably coated with sugar, gelatine or the like.

According to one embodiment, an injectable form comprising the active principle is prepared, where appropriate, by mixing the said active principle with a pH regulator, a buffer agent, a suspension agent, a solubiliser, a stabiliser, a tonicity agent and/or a preserving agent, and by converting the mixture into a form for parenteral, e.g. intravenous, subcutaneous or intramuscular, injection, according to a standard process. Where appropriate, the injectable form obtained may be freeze-dried via a standard process. Examples of suspension agents include methylcellulose, polysorbate 80, hydroxyethylcellulose, acacia, powdered gum tragacanth, sodium carboxymethylcellulose and polyethoxylated sorbitan monolaurate. Examples of solubilisers include castor oil solidified with polyoxyethylene, polysorbate 80, nicotinamide, polyethoxylated sorbitan monolaurate and the ethyl ester of castor oil fatty acid. In addition, stabilisers include sodium sulfite, sodium metasulfite and ether, whereas preserving agents include methyl p-hydroxybenzoate, ethyl p-hydroxybenzoate, sorbic acid, phenol, cresol and chlorocresol.

The present invention also relates to the use of a compound of the formula (I) of the invention for the preparation of a medicament for the prevention or treatment of dyslipidaemia, atherosclerosis and/or type II diabetes and related diseases, such as obesity and microvascular complications (e.g. nephropathy and neuropathy). The use is especially directed towards the treatment or prevention of these diseases by means of a repressive effect on CETP.

The invention also relates to a method for the treatment of or preventing these diseases, in which method an effective amount of a pharmaceutical composition or medicament according to the invention is administered to a patient in need thereof. For the implementation of such a method, the pharmaceutical composition or medicament may be administered via any suitable route, such as the oral route, the parenteral route or the topical or local route, as emerges especially from the present description.

More generally, the present invention relates to a method for the treatment of or preventing any disease, condition or state caused by or associated with the activity of CETP, to induce in the patient a repression of CETP. This method makes it possible to benefit from the positive effect of this repression on the prevention and treatment of the related diseases, such as those described above.

The effective administration doses and posologies of the compounds of the invention, intended for prevention or treatment, depend on a large number of factors, for example the size of the patient, the desired aim of the treatment, the nature of the pathology to be treated, the specific pharmaceutical composition used and the observations and conclusions of the treating doctor.

For example, in the case of an oral administration, for example a tablet or a gel capsule, a possible suitable dosage of the compound of the formula (I) (active principle) is between about 0.1 mg and about 100 mg of active principle per kg of body weight per day, preferably between about 0.5 mg/kg and about 50 mg/kg of body weight per day, more preferably between about 1 mg/kg and about 10 mg/kg of body weight per day and more preferably between about 2 mg/kg and about 5 mg/kg of body weight per day.

If representative body weights of 10 kg and 100 kg are considered in order to illustrate the daily oral dosage range that can be used and as described above, suitable dosages of the compounds of the formula (I) will be between about 1-10 mg and 1000-10 000 mg per day, preferably between about 5-50 mg and 500-5000 mg per day, more preferably between about 10.0-100.0 mg and 100.0-1000.0 mg per day, and more preferentially between about 20.0-200.0 mg and about 50.0-500.0 mg per day of active principle.

These dosage ranges represent total amounts of active principle per day for a given patient. The number of administrations per day may vary within wide proportions as a function of pharmacokinetic and pharmacological factors, such as the half-life of the active material, which reflects its rate of catabolism and of clearance, and also the minimum and optimum levels of the said active material that are reached in the blood plasma or other bodily fluids of the patient and that are required for therapeutic efficacy.

Other factors may also be considered in deciding on the number of daily administrations and on the amount of active material that should be administered in a single intake. Among these other factors, and not the least of which, is the individual response of the patient to be treated.

Figure 1:
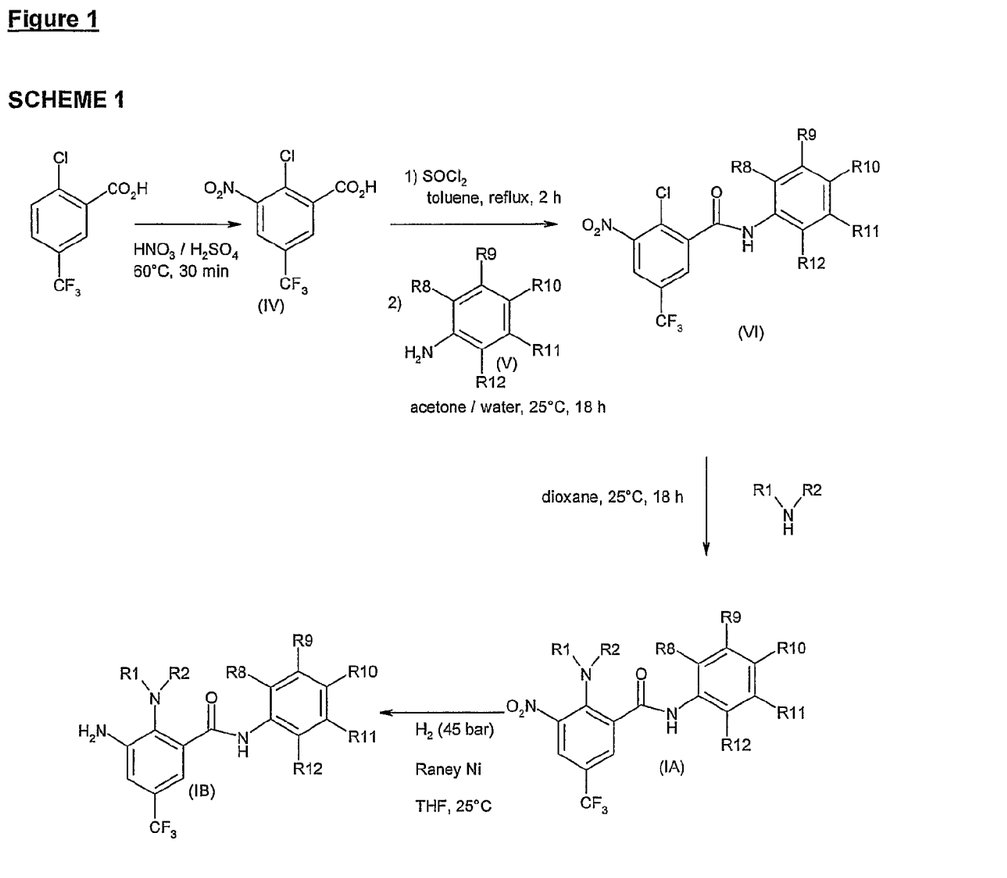
Figure 2:
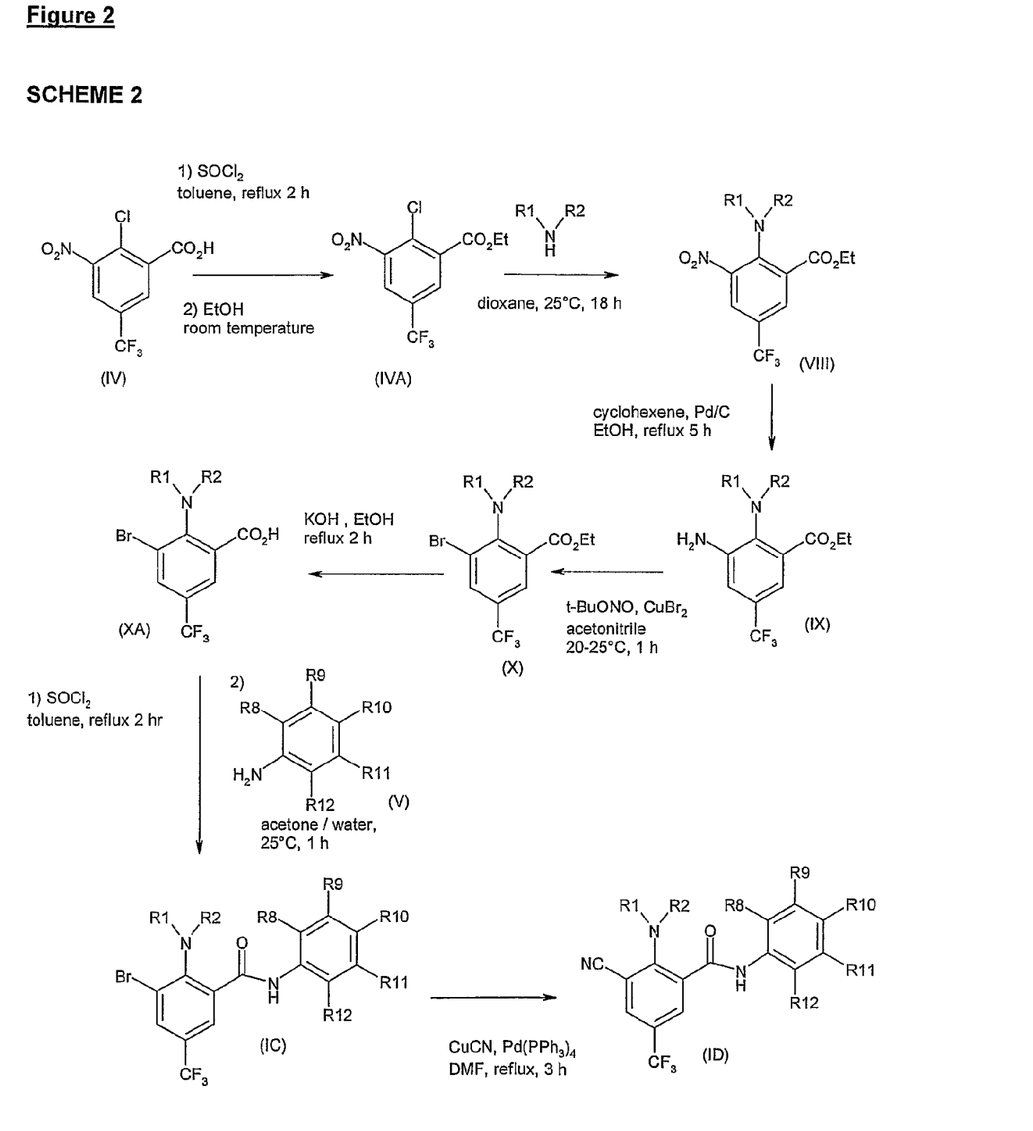
Figure 3:
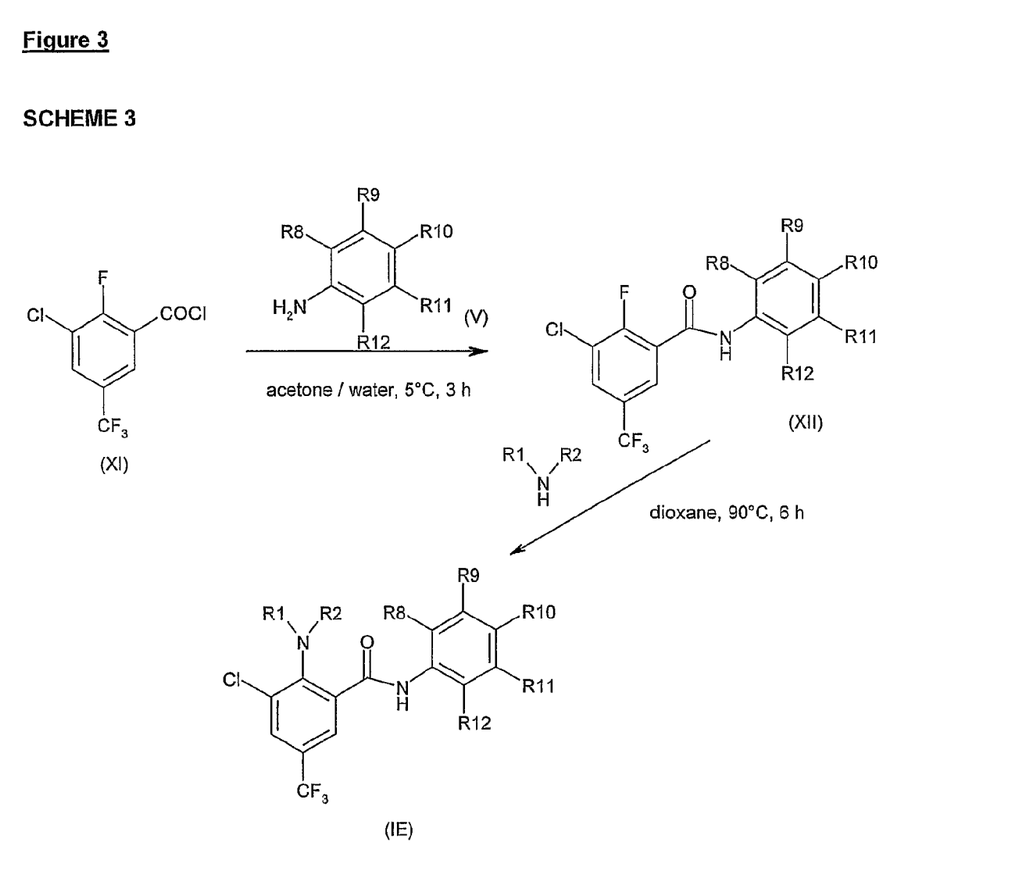

The present invention also relates to various processes for the preparation of the compounds of the formula (I), which are illustrated specifically and in detail in the synthetic schemes 1 (method A), 2 (method B) and 3 (method C) given in FIG. 1, FIG. 2 and FIG. 3, in which the various variable substituents are as defined above for the compounds of the formula (I).

Method A: this is more particularly suited to compounds of the formula (I) for which $R_3$ represents an $NH_2$ or $NO_2$ group.
In general:
- a 2-chloro-3-nitro-5-trifluoromethyl acid of the formula (IV) represented in FIG. 1 is treated with a chlorinating agent in organic solvent medium, and the resulting product is then subjected to the action of an amine AR of the formula (V), $R_8$ to $R_{12}$ being as defined above, in water/ketonic solvent medium, to give an amide of the formula (VI),
- the amide is subjected to the action of an amine $HNR_1R_2$, $R_1$ and $R_2$ being as defined above, to give the benzamide derivative of the formula (IA),
- optionally, the compound of the formula (IA) is converted into a benzamide derivative of the formula (IB) via catalytic reduction under hydrogen.

The process may be performed starting with 2-chloro-5-trifluoromethylbenzoic acid, which is treated with nitric acid in sulfuric medium to obtain the acid of the formula (IV) (Welch D. E et al., *J. Med. Chem.*, (1969), 12, pp. 299-303). This reaction is performed at elevated temperature, especially between 40 and 80° C., for example at about 60° C., for a sufficient period, for example between 15 minutes and 1 hour. The acid of the formula (IV) obtained may be recovered in solid form, for example by precipitation by cooling and optionally recrystallisation.

The acid of the formula (IV) is then treated with a chlorinating agent, such as $PCl_5$, $POCl_3$, $SOCl_2$ or $(COCl)_2$ at reflux in an aromatic solvent, such as toluene or xylene, for a sufficient period, which may range from one to several hours, for example from about 1 hour to about 3 hours (e.g. 2 hours).

The acid chloride thus obtained (optionally after evaporation of the reaction medium) is treated with an amine of the formula (V) for a sufficient period, which may range from one to several hours, for example from about 15 hours to about 24 hours (e.g. 18 hours). The reaction temperature generally ranges between 15° C. and 100° C., for example between 15° C. and 60° C. and better still at room temperature between 15° C. and 30° C. (e.g. 25° C.). The reaction is performed in a mixture comprising water and a ketonic solvent, for example acetone, preferably in a water/ketonic solvent ratio of between 0.5 and 3 and better still between 0.5 and 1.5. Preferably, a solution of amine (V) in the ketonic solvent (preferably at low temperature, e.g. 0° C.) is gradually added (e.g. dropwise) to a solution of (IV) in the water/ketonic solvent medium, and the mixture is then incubated at the desired temperature. After incubation, a solid (VI) may be precipitated, for example, by adding water. The compound of the formula (VI) is thus obtained.

The compound of the formula (VI) is then treated with an amine of the formula $HNR_1R_2$. The reaction is preferably performed in an aprotic solvent, such as a linear or cyclic ether of the type, such as ethyl ether, di-tert-butyl ether, diisopropyl ether or dimethoxyethane, or alternatively of the type, such as dioxane or tetrahydrofuran (THF), tetrahydrofuran and dioxane being preferred. The reaction temperature of the said reaction generally ranges between 20° C. and 150° C., for example between 20° C. and 120° C. and better still between 20° C. and 100° C. The compound of the formula (IA) is thus obtained. Preferably, the amine is added in a solution of (IV) in the solvent. After incubation, the benzamide derivative obtained (IA) may be recovered and then optionally converted as described below. The recovery may be performed by adding water, extracting with ethyl acetate, drying and concentrating the organic phase, dissolving in ethyl ether and ethane, and then recovering and drying the solid.

By catalytic reduction, for example in the presence of a suitable catalyst, such as Raney nickel or palladium, the benzamide derivative of the formula (IB) is obtained. More specifically, the catalyst is added to a solution of the compound of the formula (IA) in an aprotic solvent, such as THF and a hydrogenation is performed, preferably at room temperature (15-30° C., e.g. 25° C.) and at a suitable partial pressure of $H_2$, especially between 30 and 60 bar, e.g. about 45 bar. At the end of the reaction, the catalyst may be removed and compound (IB) then recovered.

This process (method A) is more particularly detailed in Examples 1 and 2.

Method B: this variant described in scheme 2 (FIG. 2) is more particularly suited to compounds of the formula (I) for which $R_3$ represents a Br or CN group.
In general:
- an amino ester of the formula (IX) represented in FIG. 2 is subjected to a Sandmeyer reaction to give the corresponding bromo ester,
- this bromo ester is converted into the acid of the formula (XA) by treatment with a base in a water/alcohol mixture,
- the acid is treated with a chlorinating agent in organic solvent medium and the resulting product is then treated with an amine AR of the formula (V), $R_8$ to $R_{12}$ being as defined above, in water/ketonic solvent medium, to give an amide of the formula (IC),
- optionally, the compound of the formula (IC) is converted into the benzamide derivative of the formula (ID) by reaction with CuCN in the presence of a transition metal-based catalyst.

The process may be performed starting with the acid chloride of the formula (IV) prepared as in method A (step 1) in the figure), which is then treated with ethanol at a temperature of about 10° C. to 50° C., for example at room temperature. The ethyl ester of the formula (IVA) is thus obtained, which may be recovered by evaporation, and then optionally purified, for example by filtration (see Example 3, step a)).

The compound of the formula (IVA) is then treated with an amine of the formula $HNR_1R_2$. The reaction is preferably performed in an aprotic solvent, such as a linear or cyclic ether of the type, such as ethyl ether, di-tert-butyl ether, diisopropyl ether or dimethoxyethane, or alternatively of the type, such as dioxane or tetrahydrofuran, tetrahydrofuran and dioxane being preferred. The incubation may last from 12 to 24 hours, e.g. about 18 hours, preferably at room temperature, between 15 and 30° C., e.g. 25° C. This step may especially be performed by adding the amine to a solution of (IVA) in the aprotic solvent. After incubation, compound (VIII) may be recovered, for example by adding water and extracting the compound with ethyl ether, followed by washing with water, drying and optionally concentrating the organic phase. The compound of the formula (VIII) is thus obtained.

By catalytic reduction of the compound of the formula (VIII), the amino compound of the formula (IX) is obtained. This reduction may be performed in the presence of a catalyst, such as Raney nickel or palladium, e.g. Pd/C (palladium supported on charcoal), especially by adding the catalyst and a solvent, such as cyclohexene to compound (VIII) in an alcohol, such as ethanol, and stirring for 1 to several (e.g. 10) hours, e.g. 5 hours, at reflux. The catalyst may then be removed, for example by filtration, and the solid optionally purified, for example by chromatography, e.g. on silica.

Compound (IX) thus obtained is then treated with tert-butyl nitrite and $CuBr_2$ in a polar solvent, for example acetonitrile, according to a Sandmeyer reaction and more particularly according to Doyle M. P., *J. Org. Chem., Vol.* 42, No 14, pp. 2426-2431 (1977). This may be performed by adding a solution of compound (IX) in the polar solvent, to a solution of tert-butyl nitrite and $CuBr_2$. The reaction temperature is preferably maintained at room temperature, between 15 and 30° C., e.g. between 20 and 25° C. The reaction is performed for a few tens of minutes, for example 1 hour, with stirring. Compound (X) is then recovered, concentrated and/or purified; for example, the medium may be poured into EtOAc, the organic phase is washed with water and then with saturated $NHCO_3$ solution, and then with brine; this is followed by drying, for example over $Na_2SO_4$, and concentrating, followed by purification by chromatography, e.g. on silica.

The compound of the formula (X) is thus obtained, which compound, by treatment with a base, such as NaOH or KOH, in an alcohol/water mixture (preferably a $C_1$-$C_4$ alcohol, such as methanol, ethanol, propanol or isopropanol, ethanol being preferred), for example ethanol/water, the said reaction being performed at elevated temperature and preferably at the reflux point of the water/alcohol mixture and preferably with stirring, to give the compound of the formula (XA). The recovery of the compound may be performed by precipitation, for example by evaporation, taking up in water, acidification, washing and drying of the precipitate.

Compound (XA) is converted into a product of the formula (IC) according to a process identical to the one described for the production of the compound of the formula (VI), method A. This benzamide derivative of the formula (IC) may be recovered and then optionally further converted as described below.

The compound of the formula (IC) is then treated with CuCN in the presence of a transition metal-based catalyst, such as Ni(0) and/or Pd(0) complexes, for example: Ni $(PPh_3)_4$, $Pd(PPh_3)_4$ and $Pd(PPh_3)_2Cl_2$, and more particularly $Pd(PPh_3)_4$ (Sakalibara Y. et al. *Bull. Chem. Soc. Jpn.,* 1988, Vol. 61, pp. 1985-1990 and EP-A-1 246 813). The copper cyanide/compound of the formula (IC) ratio may be between 0.5 and 5, more particularly between 0.5 and 3 and better still between 1 and 3, and the catalyst is preferably used in an amount corresponding to 0.5-10, preferably 2-6 and more particularly about 4-5% by weight relative to the compound of the formula (IC). The benzamide derivative of the formula (ID) is thus obtained. More specifically, the reaction may be performed as follows: CuCN and the complex are added to a solution of compound (IC) in a solvent, such as DMF; the mixture is refluxed for a few hours, e.g. 3 hours, under a nitrogen atmosphere; this may be followed by cooling, addition to water and extraction with, e.g. ethyl acetate, and steps of washing and drying of the organic phase, and optionally purification, for example by chromatography, e.g. on silica.

This process (method B) is more particularly detailed in Examples 3 and 4.

Method C: this is more particularly suited to compounds of the formula (I) for which $R_3$ represents chlorine.

In general:
an acid chloride of the formula (XI) represented in FIG. 3 is subjected to the action of an amine AR of the formula (V), $R_8$ to $R_{12}$ being as defined above, in water/ketonic solvent medium, to give an amide of the formula (XII), the amide is subjected to the action of an amine $HNR_1R_2$, $R_1$ and $R_2$ being as defined above, to give the benzamide derivative of the formula (IE).

According to this variant, 3-chloro-2-fluoro-5-(trifluoromethyl)benzoyl chloride (formula (XI)) is treated with an amine of the formula (V) for a period ranging from one to several hours, for example from about 2 hours to about 12 hours. The reaction temperature generally ranges between 0° C. and 50° C., for example between 0° C. and 20° C. and better still between 5° C. and 15° C. The reaction is performed in a mixture comprising water and a ketonic solvent, for example acetone, in a water/ketonic solvent ratio of between 0.5 and 3 and better still between 0.5 and 1.5. More specifically, the process may be performed as follows: a solution of (XI) in a ketonic solvent is gradually added, preferably dropwise, to a solution of amine in a water/ketonic solvent mixture, this solvent preferably being the same in both cases, e.g. acetone. After incubating with stirring at the chosen temperature, water may be added, especially cold water, and the white precipitate formed is then recovered, and may be further treated as described in the examples. The compound of the formula (XIII) is thus obtained.

The compound of the formula (XII) is then treated with an amine of $HNR_1R_2$. The reaction is preferably performed in an aprotic solvent, such as a linear or cyclic ether of the type, such as ethyl ether, di-tert-butyl ether, diisopropyl ether or dimethoxyethane, or alternatively of the type, such as dioxane or tetrahydrofuran, tetrahydrofuran and dioxane being preferred. The reaction temperature of the said reaction generally ranges between 20° C. and 150° C., for example between 50° C. and 120° C. and better still between 70° C. and 100° C. For example, a mixture of compound (XII) and of amine in the aprotic solvent is stirred for several hours (between 2 and 20 hours, e.g. about 6 hours) at the chosen temperature. The mixture may then be evaporated and the solid taken up in a solvent/water mixture, such as dichloromethane/water, followed by drying the organic phase, and optionally purifying, for example by chromatography, e.g. on silica. The benzamide derivative of the formula (IE) is thus obtained.

This process (method C) is more particularly detailed in Examples 5 to 11.

In the processes described above, it should be understood that the operating conditions may vary substantially as a function of the various substituents present in the compounds of the formula (I) that it is desired to prepare. Such variations and adaptations are readily accessible to those skilled in the art, for example from scientific reviews, the patent literature, Chemical Abstracts, and computer databases, including the Internet. Similarly, the starting materials are either commercially available or accessible via syntheses that a person skilled in the art may readily find, for example in the various publications and databases described above.

The possible optical isomers of the compounds of the formula (I) may be obtained on the one hand via standard techniques of separation and/or purification of isomers known to those skilled in the art, from the racemic mixture of the compound of the formula (I). The optical isomers may also be obtained directly via stereoselective synthesis of an optically active starting compound.

The examples that follow illustrate the present invention without limiting it in any way. In these examples and in the proton nuclear magnetic resonance data (300 MHz NMR), the following abbreviations have been used: letter s for singlet, d for doublet, t for triplet, q for quartet, o for octet, m for complex multiplet, and b for broad. The chemical shifts δ are expressed in ppm, unless otherwise specified. TFA means trifluoroacetic acid.

EXAMPLES

I) Method A (Scheme 1, FIG. 1):

Example 1

N-(3,4-Dichlorophenyl)-3-nitro-2-piperid-1-yl-5-trifluoromethylbenzamide

Step a): 2-Chloro-3-nitro-5-trifluoromethylbenzoic acid

After dissolving at room temperature 2-chloro-5-trifluoromethylbenzoic acid (2.25 g; 10 mmol) in fuming sulfuric acid comprising 20% oleum (6 ml), fuming nitric acid (1.7 ml) is added dropwise over 30 minutes, so as to maintain the temperature of the reaction medium below 60° C. After cooling, ice is added and the precipitate is separated out, washed with water and dried. After recrystallisation from water, 2.15 g of solid corresponding to 2-chloro-3-nitro-5-trifluoromethylbenzoic acid are obtained (m.p.=173° C.).
$^1$H NMR (300 MHz, CDCl$_3$) δ ppm: 8.41 (d, 1H), 8.71 (d, 1H), 14.30 (s, 1H)

Step b): 2-Chloro-3-nitro-5-trifluoromethylbenzoyl chloride

To a solution of 2-chloro-3-nitro-5-trifluoromethylbenzoic acid (1.35 g) in toluene (15 ml) are added 1.2 ml of SOCl$_2$. After refluxing for 2 hours, the end of the reaction is confirmed by monitoring by infrared (new band at 1788 cm$^{-1}$). The reaction medium is evaporated to dryness and the resulting yellow oil, 2-chloro-3-nitro-5-trifluoromethylbenzoyl chloride, is used without further purification in the following step.

Step c): N-(3,4-Dichlorophenyl)-2-chloro-3-nitro-5-trifluoromethylbenzamide

To a solution of 3,4-dichloroaniline (2.6 g; 2 eq.) in a 1/1 acetone/water mixture (30 ml) is added dropwise at 0° C. a solution of 2-chloro-3-nitro-5-trifluoromethylbenzoyl chloride (2.3 g; 1 eq.) in acetone (10 ml). After 18 hours at room temperature, 20 ml of water are added. The resulting solid is filtered off by suction, washed with water and dried. 3.1 g of N-(3,4-dichlorophenyl)-2-chloro-3-nitro-5-trifluoromethylbenzamide are obtained (m.p.=202° C.).
$^1$H NMR (300 MHz, CDCl$_3$) δ ppm: 7.47 (m, 2H), 7.67 (s, 1H), 7.90 (d, 1H), 8.14 (d, 1H), 8.19 (d, 1H)

Step d): N-(3,4-Dichlorophenyl)-3-nitro-2-piperid-1-yl-5-trifluoromethylbenzamide To a solution of N-(3,4-dichlorophenyl)-2-chloro-3-nitro-5-trifluoromethylbenzamide (0.76 g; 1 eq.) in dioxane (12 ml) is added piperidine (0.4 ml; 2.2 eq.). After stirring for 18 hours at 25° C., 10 ml of water are added and the product is extracted with ethyl acetate. The organic phase is dried and concentrated. The orange oil obtained is dissolved in 2 ml of ethyl ether and 120 ml of hexane. After 3 days at 0° C., the solid is filtered off by suction and dried. 540 mg of N-(3,4-dichlorophenyl)-3-nitro-2-piperid-1-yl-5-trifluoromethylbenzamide are obtained (m.p.=144° C.).
$^1$H NMR (300 MHz, CDCl$_3$) δ ppm: 1.7 (m, 6H), 3.2 (m, 4H), 7.4 (m, 2H), 7.9 (d, J=2.3 Hz, 1H), 8.0 (s, 1H), 8.5 (d, J=2.3 Hz, 1H), 10.5 (s, 1H)

Example 2

3-Amino-N-(3,4-dichlorophenyl)-2-piperid-1-yl-5-trifluoromethylbenzamide

To a solution of N-(3,4-dichlorophenyl)-3-nitro-2-piperid-1-yl-5-trifluoromethylbenzamide, Example 1 (4.15 g) in THF (80 ml), is added Raney nickel (2 g) under nitrogen. The reaction medium is hydrogenated at room temperature under a pressure of 45 bar. At the end of the reaction (stable absorption of hydrogen), the catalyst is removed and the medium is concentrated. 3.15 g of 3-amino-N-(3,4-dichlorophenyl)-2-piperid-1-yl-5-trifluoromethylbenzamide are obtained as a white solid.
$^1$H NMR (300 MHz, CDCl$_3$) δ ppm: 1.8 (m, 6H), 3.2 (m, 4H), 3.7 (m, 1H), 4.7 (broad s, 1H), 7.0 (s, 1H), 7.4 (m, 3H), 8.0 (d, J=2.3 Hz, 1H), 9.6 (s, 1H)

II) Method B (Scheme 2, FIG. 2):

Example 3

3-Bromo-N-(3,4-dichlorophenyl)-2-piperid-1-yl-5-trifluoromethylbenzamide

Step a): Ethyl 2-chloro-3-nitro-5-trifluoromethylbenzoate

The 2-chloro-3-nitro-5-trifluoromethylbenzoyl chloride (5.5 g; 18 mmol), obtained in step b) of Example 1, is dissolved in ethanol (50 ml) and stirred for 1 hour at room temperature. After evaporating to dryness, the pasty solid is purified by filtration on silica (eluent: dichloromethane). 4.2 g of ethyl 2-chloro-3-nitro-5-trifluoromethylbenzoate are obtained in the form of a pale yellow oil.
$^1$H NMR (300 MHz, CDCl$_3$) δ ppm: 1.44 (t, 3H), 4.44 (q, 2H), 8.08 (d, 1H), 8.19 (d, 1H)

Step b): Ethyl 3-nitro-2-piperid-1-yl-5-trifluoromethylbenzoate

To a solution of ethyl 2-chloro-3-nitro-5-trifluoromethylbenzoate (4.2 g; 1 eq.) in dioxane (40 ml) is added piperidine (3.9 ml; 2.1 eq.). After stirring for 18 hours at room temperature, the medium is poured into water (50 ml) and the product is extracted with ethyl ether. The organic phase is washed with water, dried and concentrated. 4.9 g of ethyl 3-nitro-2-piperid-1-yl-5-trifluoromethylbenzoate are obtained in the form of a colourless oil.
$^1$H NMR (300 MHz, CDCl$_3$) δ ppm: 1.41 (t, 3H), 1.62 (m, 6H), 3.05 (m, 4H), 4.41 (q, 2H), 7.84 (d, 1H), 7.88 (d, 1H)

Step c): Ethyl 3-amino-2-piperid-1-yl-5-trifluoromethylbenzoate

To a solution of ethyl 3-nitro-2-piperid-1-yl-5-trifluoromethylbenzoate (4.9 g; 1 eq.) in ethanol (50 ml) are added cyclohexene (10.5 ml; 7.5 eq.) and 10% Pd/C (0.6 g), and the mixture is stirred at reflux for 5 hours. After removing the catalyst by filtration and concentrating to dryness, the pasty solid is purified by chromatography on silica (eluent: 4/1 pentane/ether). 2.15 g of ethyl 3-amino-2-piperid-1-yl-5-trifluoromethylbenzoate are obtained in the form of a reddish oil.

$^1$H NMR (300 MHz, CDCl$_3$) δ ppm: 1.43 (t, 3H), 1.64 (s, 2H), 2.74 (m, 6H), 4.30 (s, 4H), 4.38 (q, 2H), 7.02 (d, 1H), 7.12 (d, 1H)

Step d): Ethyl 3-bromo-2-piperid-1-yl-5-trifluoromethylbenzoate

To a solution of t-butyl nitrite (1.7 ml; 1.9 eq.) and CuBr$_2$ (3.25 g; 2.15 eq.) in acetonitrile (25 ml) is added a solution of ethyl 3-amino-2-piperid-1-yl-5-trifluoromethylbenzoate (2.15 g; 1 eq.) in acetonitrile (14 ml), while maintaining the temperature between 20 and 25° C. After stirring for one hour at this temperature, the medium is poured into EtOAc and the organic phase is washed with water, with saturated NaHCO$_3$ and then with brine. After drying over Na$_2$SO$_4$ and concentrating under vacuum, the pasty solid is purified by chromatography on silica (eluent: 9/1 hexane/EtOAc). 830 mg of ethyl 3-bromo-2-piperid-1-yl-5-trifluoromethylbenzoate are obtained in the form of a beige-coloured oil.

$^1$H NMR (300 MHz, CDCl$_3$) δ ppm: 1.40 (t, 3H), 1.67 (m, 6H), 3.07 (s, 4H), 4.38 (q, 2H), 7.68 (d, 1H), 7.88 (d, 1H)

Step e): 3-Bromo-2-piperid-1-yl-5-trifluoromethylbenzoic acid

To a solution of ethyl 3-bromo-2-piperid-1-yl-5-trifluoromethylbenzoate (830 mg; 1 eq.) in ethanol (30 ml) is added potassium hydroxide (610 mg; 5 eq.). After stirring at reflux for 2 hours, the reaction medium is evaporated to dryness, taken up in water (20 ml) and acidified with 1N HCl. The precipitate is filtered off by suction, washed with water and dried. 600 mg of 3-bromo-2-piperid-1-yl-5-trifluoromethylbenzoic acid are obtained in the form of a white solid.

$^1$H NMR (300 MHz, DMSO-d6) δ ppm: 1.58 (m, 3H), 1.64 (m, 3H), 3.08 (m, 4H), 7.84 (d, 1H), 8.09 (d, 1H), 14.07 (s, 1H)

Step f): 3-Bromo-N-(3,4-dichlorophenyl)-2-piperid-1-yl-5-trifluoromethylbenzamide To a solution of 3-bromo-2-piperid-1-yl-5-trifluoromethylbenzoic acid (680 mg; 1 eq.) in toluene (15 ml) is added SOCl$_2$ (0.55 ml). After refluxing for 2 hours, the reaction medium is evaporated to dryness and the oil obtained is taken up in acetone (5 ml). This solution is added dropwise, while maintaining the temperature between 15 and 20° C., to a solution of 3,4-dichloroaniline (625 mg; 2 eq.) in water (7 ml) and acetone (10 ml). After stirring for 1 hour at room temperature, the precipitate is filtered off by suction, washed with water and dried. 820 mg of 3-bromo-N-(3,4-dichlorophenyl)-2-piperid-1-yl-5-trifluoromethylbenzamide are obtained in the form of a white solid.

$^1$H NMR (300 MHz, CDCl$_3$) δ ppm: 1.8 (m, 6H) 3.4 (m, 4H) 7.5 (m, 2H) 7.9 (d, J=1.5 Hz, 1H) 8.0 (d, J=2.3 Hz, 1H) 8.5 (d, J=1.5 Hz, 1H) 12.4 (s, 1H)

Example 4

3-Cyano-N-(3,4-dichlorophenyl)-2-piperid-1-yl-5-trifluoromethylbenzamide

To a solution of 3-bromo-N-(3,4-dichlorophenyl)-2-piperid-1-yl-5-trifluoromethylbenzamide, Example 3 (620 mg; 1 eq.) in DMF (10 ml, degassed for 1 hour with nitrogen), are added CuCN (200 mg; 1.8 eq.) and Pd(PPh$_3$)$_4$ (58 mg; 0.04 eq.). After refluxing for 3 hours under a nitrogen atmosphere, the reaction medium is cooled and poured into 20 ml of water. The product is extracted with ethyl acetate. After washing with water and then with saturated NaCl solution, the organic phase is dried over Na$_2$SO$_4$ and concentrated under vacuum. The oil obtained is purified by chromatography on silica (eluent: 9/1 heptane/EtOAc). 310 mg of 3-cyano-N-(3,4-dichlorophenyl)-2-piperid-1-yl-5-trifluoromethylbenzamide are obtained (white solid: m.p.=175° C.)

$^1$H NMR (300 MHz, CDCl$_3$) δ ppm: 1.8 (m, 6H) 3.4 (m, 4H) 7.5 (m, 2H) 8.0 (m, 2H) 8.7 (d, J=1.9 Hz, 1H) 11.7 (s, 1H)

III) Method C (Scheme 3, FIG. 3):

Step a): General procedure for the preparation of N-aryl-3-chloro-2-fluoro-5-trifluoromethylbenzamide To a solution of arylamine (20 mmol; 2 eq.) in a 2/1 acetone/water mixture (60 ml) is added dropwise, at 5° C., a solution of 3-chloro-2-fluoro-5-trifluoromethylbenzoyl chloride (2.68 g; 1 eq.) in acetone (40 ml). After stirring for 3 hours at 5° C., 120 ml of cold water are added. The white precipitate of N-aryl-3-chloro-2-fluoro-5-trifluoromethylbenzamide is filtered off by suction, rinsed with water and then with heptane, and dried under vacuum.

Step b): General procedure for the preparation of N-aryl-3-chloro-2-(cycloalkylamino)-5-trifluoromethylbenzamide A mixture of N-aryl-3-chloro-2-fluoro-5-trifluoromethylbenzamide (1.7 mmol; 1 eq.) and of cycloalkylamine of the formula (II) (3.4 mmol; 2 eq.) dissolved in dioxane (28 ml) is stirred for 6 hours at 90° C. After evaporating to dryness and taking up in a dichloromethane/water mixture, the organic phase is dried over Na$_2$SO$_4$. After concentrating, the N-aryl-3-chloro-2-(cycloalkylamino)-5-trifluoromethylbenzamide is purified by chromatography on silica (eluent: 3/1 heptane/EtOAc).

The compounds of Examples 5-11 below were prepared according to the general procedure described above, using 3,4-dichloroaniline as arylamine and the indicated cycloalkylamine.

Example 5

2-Azepan-1-yl-3-chloro-N-(3,4-dichlorophenyl)-5-trifluoromethylbenzamide

Cycloalkylamine: azepane $^1$H NMR (300 MHz, CDCl$_3$) δ ppm: 1.8 (m, 4H), 1.9 (m, 4H), 3.4 (m, 4H), 7.5 (m, 2H), 7.8 (d, J=1.9 Hz, 1H), 7.9 (d, J=2.3 Hz, 1H), 8.6 (d, J=2.3 Hz, 1H), 12.7 (s, 1H)

Example 6

3-Chloro-N-(3,4-dichlorophenyl)-2-(4-methylpiperid-1-yl)-5-trifluoromethylbenzamide Cycloalkylamine: 4-methylpiperidine $^1$H NMR (300 MHz, CDCl$_3$) δ ppm: 1.1 (d, J=6.4 Hz, 3H), 1.6 (m, 5H), 3.1 (m, 2H), 3.7 (m, 2H), 7.4 (d, J=8.7 Hz, 1H), 7.6 (dd, J=8.7 2.6 Hz, 1H), 7.7 (d, J=2.3 Hz, 1H), 8.0 (d, J=2.3 Hz, 1H), 8.6 (s, 1H), 13.1 (m, 1H)

Example 7

3-Chloro-N-(3,4-dichlorophenyl)-2-(4-hydroxy-4-phenylpiperid-1-yl)-5-trifluoromethylbenzamide

Cycloalkylamine: 4-hydroxy-4-phenylpiperidine
$^1$H NMR (300 MHz, CDCl$_3$) δ ppm: 1.7 (m, 1H), 2.0 (m, 2H), 2.3 (m, 2H), 3.1 (m, 2H), 4.3 (m, 2H), 7.3 (m, 1H), 7.4 (m, 3H), 7.5 (m, 2H), 7.6 (dd, J=8.7 2.3 Hz, 1H), 7.8 (d, J=1.9 Hz, 1H), 7.8 (d, J=1.9 Hz, 1H), 8.5 (m, 1H), 13.1 (m, 1H)

Example 8

Methyl 1-[2-chloro-6-(((3,4-dichlorophenyl)amino)carbonyl)-4-(trifluoromethyl)phenyl]piperidine-4-carboxylate

Cycloalkylamine: 4-(trifluoromethylphenyl)piperidine
For step b) of this example, 6 equivalents of methyl 4-piperidinecarboxylate were reacted for 18 hours.
$^1$H NMR (300 MHz, CDCl$_3$) δ ppm: 2.0 (m, 4H), 2.6 (m, 1H), 3.2 (m, 2H), 3.7 (m, 2H), 3.8 (s, 3H), 7.4 (d, J=9.0 Hz, 1H), 7.6 (m, 1H), 7.7 (d, J=1.9 Hz, 1H), 8.1 (d, J=1.9 Hz, 1H), 8.5 (m, 1H), 12.7 (m, 1H)

Example 9

3-Chloro-N-(3,4-dichlorophenyl)-2-(4-hydroxymethylpiperid-1-yl)-5-trifluoromethylbenzamide

Cycloalkylamine: 4-(hydroxymethyl)piperidine
$^1$H NMR (300 MHz, CDCl$_3$) δ ppm: 1.7 (m, 3H), 1.9 (m, 2H), 3.2 (m, 2H), 3.7 (d, J=4.9 Hz, 2H), 3.78 (m, 2H), 7.4 (d, J=8.7 Hz, 1H), 7.7 (m, 2H), 8.0 (d, J=2.6 Hz, 1H), 8.6 (m, 1H), 13.0 (s, 1H)

Example 10

3-Chloro-N-(3,4-dichlorophenyl)-2-(3,5-dimethylpiperid-1-yl)-5-trifluoromethylbenzamide

Cycloalkylamine: 3,5-dimethylpiperidine
$^1$H NMR (300 MHz, CDCl$_3$) δ ppm: 0.9 (m, 1H), 1.0 (d, J=6.4 Hz, 6H), 1.9 (m, 3H), 3.0 (m, 2H), 3.3 (t, J=11.1 Hz, 2H), 7.4 (m, 2H), 7.7 (m, 1H), 8.0 (d, J=1.5 Hz, 1H), 8.6 (s, 1H), 12.8 (m, 1H)

Example 11

3-Chloro-N-(3,4-dichlorophenyl)-2-(octahydroisoguinol-2(1H)yl)-5-trifluoromethylbenzamide

Cycloalkylamine: decahydroisoquinoline
$^1$H NMR (300 MHz, CDCl$_3$) δ ppm: 1.4 (m, 7H), 1.9 (m, 5H), 2.9 (m, 2H), 3.6 (m, 2H), 7.5 (m, 2H), 7.7 (m, 1H), 8.0 (m, 1H), 8.6 (m, 1H), 13.3 (s, 1H)

Results
In Vitro Screening Test
Measurement of an inhibitory effect on the activity of CETP (cholesteryl ester transfer protein)

The measurement of the CETP activity is performed by measuring the transfer of $^3$H-cholesterol ester from the HDLs to the biotinylated LDLs.

The transfer is measured after incubation for 24 hours in the presence of donor (HDL), acceptor (LDL) and CETP, with or without inhibitor. The reaction is stopped and the transfer measured by addition of SPA streptavidin beads (Amersham).

The increase in scintillation is proportional to the transfer of $^3$H-cholesterol ester via CETP to the LDLs.

To perform the test, 10 μl of $^3$H-cholesterol ester HDL, 10 μl of biotinylated LDL and 10 μl of HEPES buffer (50 mM HEPES/0.15 mM NaCl/0.1% BSA/0.05% NaN$_3$, pH 7.4) are mixed with 10 μl of CETP (1 mg/ml) and the test product (1 μl of the stock solution at 10 mM in DMSO) or 1 μl of DMSO alone in a 96-well microplate (Costar).

Screening is performed at a final concentration of 10 μM per well in 0.1% of solvent.

The plates are then covered with a film, shaken and incubated under a humid atmosphere at 37° C. for 24 hours.

200 μl of SPA-streptavidin beads solution (Amersham, TRKQ 7005) are added and the radioactivity reading is taken 1 hour later on a scintillation counter (Top Count, Packard) with a reading time of 0.5 minute.

The inhibition results are expressed relative to the control test (CETP+solvent).

The IC 50 values are determined and expressed in μM.

For all the Examples 1 to 11, the inhibition is greater than 50% at 10 μM.

| Example | Name | IC50 (μM) |
|---|---|---|
| 1 | N-(3,4-dichlorophenyl)-3-nitro-2-piperid-1-yl-5-trifluoromethylbenzamide | 1.45 |
| 2 | 3-Amino-N-(3,4-dichlorophenyl)-2-piperid-1-yl-5-trifluoromethylbenzamide | 0.93 |
| 3 | 3-Bromo-N-(3,4-dichlorophenyl)-2-piperid-1-yl-5-trifluoromethylbenzamide | 0.89 |
| 6 | 3-Chloro-N-(3,4-dichlorophenyl)-2-(4-methylpiperid-1-yl)-5-trifluoromethylbenzamide | 0.75 |

It should be clearly understood that the invention defined by the appended claims is not limited to the particular embodiments indicated in the above description, but rather covers all the variants that do not depart either from the scope or from the spirit of the present invention.

The invention claimed is:
1. A compound of formula (I):

in which:
R$_1$ and R$_2$, which may be identical or different, are a (C$_1$-C$_6$)alkyl radical or a (C$_3$-C$_{10}$)cycloalkyl radical, or alternatively
the two radicals R$_1$ and R$_2$ together form, with the nitrogen atom that bears them, a saturated heterocyclic radical of formula (II):

in which:
Y and Z, which may be identical or different, are C$_1$, C$_2$ or C$_3$ hydrocarbon-based chains, optionally substituted by one or more radicals R$_4$, which may be identical or different, selected from the group consisting of ($C_1$-$C_6$) alkyl and ($C_3$-$C_{10}$)cycloalkyl, X is a carbon, oxygen or sulfur atom, a group >$CR_6R_7$ with $R_6$ and $R_7$, which may be identical or different, representing OH, a group —COOAlk, Alk meaning $C_1$-$C_6$ alkyl, a —$CH_2$OH group, a substituted or unsubstituted ($C_6$-$C_{18}$)aryl radical, a substituted or unsubstituted ($C_6$-$C_{18}$)aroyl radical, a group N—$R_5$ with $R_5$ being a ($C_1$-$C_6$)alkyl radical, or alternatively the two radicals $R_1$ and $R_2$ together from, with the nitrogen atom that bears them, a tetrahydroisoquinolyl radical $R_3$ is $NO_2$, $NH_2$, CN, Cl or Br AR is a substituted or unsubstituted ($C_6$-$C_{18}$)aryl radical of formula (III):

(III)

in which $R_8$, $R_9$, $R_{10}$, $R_{11}$ and $R_{12}$, which may be identical or different, are selected from the group consisting of a hydrogen atom, a halogen atom, a branched or unbranched ($C_1$-$C_{10}$)alkyl radical, a substituted or unsubstituted aryl radical, a CN radical and a trifluoromethyl group, or alternatively $R_8$ and $R_9$ or $R_9$ and $R_{10}$ or $R_{10}$ and $R_{11}$ or $R_{11}$ and $R_{12}$ together form a chain —($CH_2$)$_p$ with p=1-5, an optical isomer, oxide form thereof, or a pharmaceutically acceptable addition salt thereof with an acid or base.

2. A compound according to claim, 1 in which $R_1$ and $R_2$ form with the nitrogen one of the following groups:

3. A compound according to claim 1, in which $R_3$ represents $NO_2$, $NH_2$, CN, Cl or Br.

4. A compound according to claim 1, in which AR represents a radical of formula (III):

(III)

with $R_8$, $R_9$ and $R_{12}$ representing hydrogen;
and $R_{10}$ and $R_{11}$ representing chlorine.

5. A compound according to claim 1, in which:

$R_1$ and $R_2$ form with the nitrogen one of the following groups:

$R_3$ represents $NO_2$, $NH_2$, CN, Cl or Br;
AR represents the radical of formula (III):

(III)

with $R_8$, $R_9$ and $R_{12}$ representing hydrogen;
and $R_{10}$ and $R_{11}$ representing chlorine.

6. A compound according to claim 1, which is
N-(3,4-dichlorophenyl)-3-nitro-2-piperid-1-yl-5-trifluoromethylbenzamide;
3-amino-N-(3,4-dichlorophenyl)-2-piperid-1-yl-5-trifluoromethylbenzamide;
3-bromo-N-(3,4-dichlorophenyl)-2-piperid-1-yl-5-trifluoromethylbenzamide;
3-cyano-N-(3,4-dichlorophenyl)-2-piperid-1-yl-5-trifluoromethylbenzamide;
2-azepan-1-yl-3-chloro-N-(3,4-dichlorophenyl)-5-trifluoromethylbenzamide;
3-chloro-N-(3,4-dichlorophenyl)-2-(4-methylpiperid-1-yl)-5-trifluoromethylbenzamide;
3-chloro-N-(3,4-dichlorophenyl)-2-(4-hydroxy-4-phenylpiperid-1-yl)-5-trifluoromethylbenzamide;
methyl-1-[2-chloro-6-(((3,4-dichlorophenyl)amino)carbonyl)-4-(trifluoromethyl)phenyl]-piperidine-4-carboxylate;
3-chloro-N-(3,4-dichlorophenyl)-2-(4-hydroxymethylpiperid-1-yl)-5-trifluoromethylbenzamide;
3-chloro-N-(3,4-dichlorophenyl)-2-(3,5-dimethylpiperid-1-yl)-5-trifluoromethylbenzamide; or
3-chloro-N-(3,4-dichlorophenyl)-2-(octahydroisoquinol-2(1H)yl)-5-trifluoromethylbenzamide.

7. A pharmaceutical composition comprising a pharmaceutically effective amount of at least one compound of the formula (I) according to claim 1, and a pharmaceutically acceptable vehicle or excipient.

8. A method for treating diabetic nephropathy, comprising administering to a subject in need thereof an effective amount of a compound of claim 1.

9. A method for treating diabetic nephropathy, comprising administering to a subject in need thereof an effective amount of a compound of claim 5.

10. A method for treating diabetic nephropathy comprising administering to a subject in need thereof an effective amount of a compound of claim 6.

11. A compound of formula (1) according to claim 1, in which:
$R_1$ and $R_2$, which may be identical or different, are a ($C_1$-$C_6$)alkyl radical or a ($C_3$-$C_{10}$)cycloalkyl radical, or alternatively
the two radicals $R_1$ and $R_2$ together form, with the nitrogen atom that bears them, a saturated heterocyclic radical of formula (II):

(II)

in which:
Y and Z, which may be identical or different, are $C_1$, $C_2$ or $C_3$ hydrocarbon-based chains, optionally substituted by one or more radicals $R_4$, which may be identical or different, selected from the group consisting of ($C_1$-$C_6$) alkyl and ($C_3$-$C_{10}$)cycloalkyl, X is a carbon, oxygen or sulfur atom, a group >$CR_6R_7$ with $R_6$ and $R_7$, which may be identical or different, representing OH, a group —COOAlk, Alk meaning $C_1$-$C_6$ alkyl, a —CH$_2$OH group, a substituted or unsubstituted ($C_6$-$C_{18}$)aryl radical, a substituted or unsubstituted ($C_6$-$C_{18}$)aroyl radical, a group N-$R_5$ with $R_5$ being a ($C_1$-$C_6$)alkyl radical, or alternatively
the two radicals $R_1$ and $R_2$ together form, with the nitrogen atom that bears them, a tetrahydroisoquinolyl radical
$R_3$ is $NO_2$, $NH_2$, CN, Cl or Br
AR is a substituted or unsubstituted ($C_6$-$C_{18}$)aryl radical of formula (III):

(III)

in which $R_8$, $R_9$, $R_{10}$, $R_{11}$ and $R_{12}$, which may be identical or different, are selected from the group consisting of a hydrogen atom, a halogen atom, a branched or unbranched ($C_1$-$C_{10}$)alkyl radical, a substituted or unsubstituted aryl radical, a CN radical and a trifluoromethyl group, or alternatively
$R_8$ and $R_9$ or $R_9$ and $R_{10}$ or $R_{10}$ and $R_{11}$ or $R_{11}$ and $R_{12}$ together form a chain —$(CH_2)_p$ with p=1-5,
or a the pharmaceutically acceptable salt thereof.

12. A process for preparing of compound of formula (I) according to claim 1, in which $R_3$ represents $NH_2$ or $NO_2$, comprising
treating a 2-chloro-3-nitro-5-trifluoromethyl acid of the formula (IV)

(IV)

with a chlorinating agent in organic solvent medium, and the resulting product is then subjected to the action of an amine AR of formula (V), (V)

$R_8$ to $R_{12}$ being as defined for the compound of formula (I), in water/ketonic solvent medium, to give an amide of the formula (VI)

(VI)

the amide is subjected to the action of an amine $HNR_1R_2$, $R_1$ and Br being as defined for the compound of formula (I) to give the benzamide compound of formula (IA)

(IA)

13. A process according to claim 12, further comprising converting the compound of the formula (IA) into a benzamide compound of formula (IB)

(IB)

via catalytic reduction under hydrogen.

14. A process for the preparing of formula (I) according to claim 1, in which $R_3$ represents Br or CN, comprising
subjecting an amino ester of the formula (IX)

(IX)

to a Sandmeyer reaction in the presence of $CuBr_2$ to give the corresponding bromo ester,
converting said bromo ester into an acid of formula (XA)

(XA)

by treatment with a base in a water/alcohol mixture,
treating said acid with a chlorinating agent in an organic solvent medium and the resulting product is then treated with an amine AR of formula (V),

(V)

$R_8$ to $R_{12}$ being as defined for the compound of formula (1), in a water/ketonic solvent medium, to give an amide of the formula (IC)

(IC)

15. A process according to claim 14, further comprising converting the compound of formula (IC) into a benzamide compound of formula (ID)

(ID)

by reaction with CuCN in the presence of a transition metal-based catalyst.

16. A process for preparing a compound of formula (I) according to claim 1, in which $R_3$ represents Cl, comprising
subjecting an acid chloride of the formula (XI)

(XI)

to the action of an amine AR of the formula (V)

(V)

$R_8$ to $R_{12}$ being as defined for the compound of formula (I), in water/ketonic solvent medium, to give an amide of the formula (XII)

subjecting said amide to the action of an amine $HNR_1R_2$, $R_1$ and $R_2$ being as defined for the compound of formula (I), to give the benzamide compound of formula (IE).

17. A method for treating diabetic nephropathy, comprising administering to a subject in need thereof an effective amount of a compound of claim 11.

18. A compound according to claim 1, which is
N-(3,4-dichlorophenyl)-3-nitro-2-piperid-1-yl-5-trifluoromethylbenzamide;
3-amino-N-(3,4-dichlorophenyl)-2-piperid-1-yl-5-trifluoromethylbenzamide;
3-bromo-N-(3,4-dichlorophenyl)-2-piperid-1-yl-5-trifluoromethylbenzamide;
3-cyano-N-(3,4-dichlorophenyl)-2-piperid-1-yl-5-trifluoromethylbenzamide;
2-azepan-1-yl-3-chloro-N-(3,4-dichlorophenyl)-5-trifluoromethylbenzamide;
3-chloro-N-(3,4-dichlorophenyl)-2-(4-methylpiperid-1-yl)-5-trifluoromethylbenzamide;
3-chloro-N-(3,4-dichlorophenyl)-2-(4-hydroxy-4-phenylpiperid-1-yl)-5-trifluoromethylbenzamide;
methyl-1-[2-chloro-6-(((3,4-dichlorophenyl)amino)carbonyl)-4-(trifluoromethyl)phenyl]-piperidine-4-carboxylate;
3-chloro-N-(3,4-dichlorophenyl)-2-(4-hydroxymethylpiperid-1-yl)-5-trifluoromethylbenzamide;
3-chloro-N-(3,4-dichlorophenyl)-2-(3,5-dimethylpiperid-1-yl)-5-trifluoromethylbenzamide; or
3-chloro-N-(3,4-dichlorophenyl)-2-(octahydroisoquinol-2(1H)yl)-5-trifluoromethylbenzamide
or a pharmaceutically acceptable salt thereof.

19. A compound according to claim 1, which is
N-(3,4-dichlorophenyl)-3-nitro-2-piperid-1-yl-5-trifluoromethylbenzamide
3-Amino-N-(3,4-dichlorophenyl)-2-piperid-1-yl-5-trifluoromethylbenzamide
3-Bromo-N-(3,4-dichlorophenyl)-2-piperid-1-yl-5-trifluoromethylbenzarnide
3-Chloro-N-(3,4-dichlorophenyl)-2-(4-methylpiperid-1-yl) -5-trifluoromethylbenzamide.

20. A method for treating diabetic nephropathy, comprising administering to a subject in need thereof an effective amount of a compound of claim 19.

* * * * *

UNITED STATES PATENT AND TRADEMARK OFFICE
CERTIFICATE OF CORRECTION

| | | |
|---|---|---|
| PATENT NO. | : 7,947,675 B2 | Page 1 of 1 |
| APPLICATION NO. | : 11/908712 | |
| DATED | : May 24, 2011 | |
| INVENTOR(S) | : Bruno Roux et al. | |

It is certified that error appears in the above-identified patent and that said Letters Patent is hereby corrected as shown below:

Title Page (75) Inventors reads: "Bruno Roux, Lyons (FR); Isabelle" should read --Bruno Roux, Lyon (FR);--.

Column 19, Line 10 reads: "the two radicals $R_1$ and $R_2$ together from, with the nitrogen" should read --the two radicals $R_1$ and $R_2$ together form, with the nitrogen--.

Column 19, Line 35 reads: "base." should read --a base.--.

Column 22, Line 19 reads: "12. A process for preparing of compound of formula (I)" should read --12. A process for preparing a compound of formula (I)--.

Column 23, Line 33 reads: "14. A process for the preparing of formula (I) according to" should read --14. A process for preparing a compound of formula (I) according to--.

Signed and Sealed this
Twenty-third Day of August, 2011

David J. Kappos
*Director of the United States Patent and Trademark Office*